US009267099B2

(12) United States Patent
Glazier et al.

(10) Patent No.: US 9,267,099 B2
(45) Date of Patent: Feb. 23, 2016

(54) ENGINEERED LUMENIZED VASCULAR NETWORKS AND SUPPORT MATRIX

(75) Inventors: James A. Glazier, Bloomington, IN (US); Abdelkrim Alileche, Boise, ID (US); Abbas Shrinifard, Bloomington, IN (US); Dragos Amarie, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 58 days.

(21) Appl. No.: 13/635,043

(22) PCT Filed: Mar. 15, 2011

(86) PCT No.: PCT/US2011/028492
§ 371 (c)(1),
(2), (4) Date: Sep. 14, 2012

(87) PCT Pub. No.: WO2011/115974
PCT Pub. Date: Sep. 22, 2011

(65) Prior Publication Data
US 2013/0004469 A1    Jan. 3, 2013

Related U.S. Application Data

(60) Provisional application No. 61/313,886, filed on Mar. 15, 2010.

(51) Int. Cl.
*C12M 1/00*    (2006.01)
*C12N 5/00*    (2006.01)
*C12N 5/02*    (2006.01)
*C12M 3/00*    (2006.01)
*C12M 1/22*    (2006.01)

(52) U.S. Cl.
CPC ............... *C12M 21/08* (2013.01); *C12M 23/10* (2013.01); *C12M 23/20* (2013.01)

(58) Field of Classification Search
None
See application file for complete search history.

(56) References Cited

U.S. PATENT DOCUMENTS 5,695,996 A * 12/1997 Quinn et al. .................. 435/367
5,750,329 A * 5/1998 Quinn et al. .................. 435/1.1
(Continued)

OTHER PUBLICATIONS

PCT International Search Report and Written Opinion issued in connection with PCT/US2011/028492 and completed by the U.S. Searching Authority on Apr. 13, 2011.
(Continued)

*Primary Examiner* — Blaine Lankford
*Assistant Examiner* — Thomas J Visone
(74) *Attorney, Agent, or Firm* — Barnes & Thornburg LLP (57) ABSTRACT

Disclosed herein are capillary fabrication devices comprising living cells within a support medium. Culture of the cells produces viable lumenized capillary networks with natural or pre-determined geometries and ECM and basement membrane associated with the capillary networks. The capillary networks and the ECM and basement membrane detachable from the capillary networks are useful for tissue engineering applications.

13 Claims, 6 Drawing Sheets

(56) References Cited

U.S. PATENT DOCUMENTS

| | | | |
|---|---|---|---|
| 6,053,939 A * | 4/2000 | Okuda et al. | 623/1.43 |
| 6,379,383 B1 * | 4/2002 | Palmaz et al. | 623/1.49 |
| 6,537,310 B1 * | 3/2003 | Palmaz et al. | 623/1.13 |
| 6,555,124 B1 * | 4/2003 | Kolter et al. | 424/434 |
| 6,579,322 B1 * | 6/2003 | Hsu et al. | 623/23.76 |
| 2001/0001834 A1 * | 5/2001 | Palmaz et al. | 623/1.15 |
| 2001/0032013 A1 * | 10/2001 | Marton | 623/1.15 |
| 2004/0234510 A1 * | 11/2004 | Mochitate | 424/93.7 |
| 2006/0263878 A1 * | 11/2006 | Mochitate | 435/366 |
| 2009/0043380 A1 * | 2/2009 | Blaha et al. | 623/1.46 |
| 2010/0041134 A1 | 2/2010 | Forgacs et al. | |
| 2010/0185281 A1 * | 7/2010 | Daphna | 623/5.11 |

OTHER PUBLICATIONS

Takei, et al. "Fabrication of Artificial Endothelialized Tubes with Predetermined Three-Dimensional Configuration from Flexible Cell-Enclosing Alginate Fibers" Biotechnol. Prog. 2007, Jan.-Feb. 2007., vol. 23, No. 1, pp. 182-186, Especially Abstract, p. 183, Figs. 1A-D.

Ino, et al. "Application of Ultra-Water-Repellent Surface to Cell Culture" J. Biosci Bioeng. Nov. 2007, vol. 104, No. 5, pp. 420-423. Especially Abstract.

* cited by examiner

ENGINEERED LUMENIZED VASCULAR
NETWORKS AND SUPPORT MATRIX

CROSS REFERENCE TO RELATED APPLICATIONS

This application is a U.S. national counterpart application of international application serial No. PCT/US2011/028492, filed Mar. 15, 2011, which claims the benefit of U.S. Provisional Patent Application No. 61/313,886, filed Mar. 15, 2010. The entire disclosures of PCT/US2011/028492 and U.S. Ser. No. 61/313,886 are hereby incorporated by reference.

STATEMENT REGARDING FEDERALLY SPONSORED RESEARCH OR DEVELOPMENT

This invention was made with government support under GM076692 awarded by the National Institutes of Health. The Government has certain rights in the invention.

FIELD

This disclosure generally relates to the field of biomedical tissue engineering. More specifically, the disclosure relates to devices for the synthesis of capillary networks with natural or controlled geometries and their associated extracellular matrix and basement membrane.

BACKGROUND AND SUMMARY

Under the proper conditions, endothelial cells or their precursors/progenitor cells, spontaneously assemble into networks and differentiate to form lumenized connected capillary networks.

Both the forming capillary network and the final capillary network and its associated extracellular matrix (ECM) have numerous scientific, industrial and medical applications. In vitro angiogenesis assays employing the forming capillary network (or capillary fabrication devices) play a crucial role in identifying factors involved in vascular development. Such assays are used in drug development as moderate-throughput screens for angiogenesis promoters and inhibitors related to wound healing, age-related macular degeneration, diabetes, cancer, and other diseases.

The completed networks formed by in vitro angiogenesis devices are also important in tissue engineering, as vascular replacements for human implantation, while the ECM of the networks can be employed as a scaffold implanted into patients to promote the growth of the patient's own vasculature into the pattern provided by the ECM.

Drug development and tissue engineering applications both require rapid creation of viable lumenized capillary networks having properties as close as possible to in vivo capillary networks. Existing in vitro angiogenesis techniques are not capable of rapidly creating lumenized capillary networks with properties substantially similar to in vivo networks.

Current methods of tissue engineering are limited to relatively thin and/or avascular tissues like skin, cartilage, and bladder, where post-implantation vascularization from the host is sufficient to meet the implant's demand for oxygen and nutrients. Vascularization remains a critical obstacle for engineering thicker, metabolically demanding organs, such as heart and liver. Thus the survival of tissue-engineered three-dimensional constructs in vivo depends on providing enough blood supply to the engineered tissue and the capacity of the engineered microcirculation to connect with the existing circulation of the recipient.

Engineering thicker, metabolically demanding organs, such as heart and liver, requires techniques for manufacturing microvessels with highly controlled geometries. Existing microcirculation engineering techniques are not capable of constructing controlled-geometry microvessels capable of connection to the host vessels, expansion of vascular volume accompanying growing tissue, and prevention of excessive vascular regression.

Figure 4:
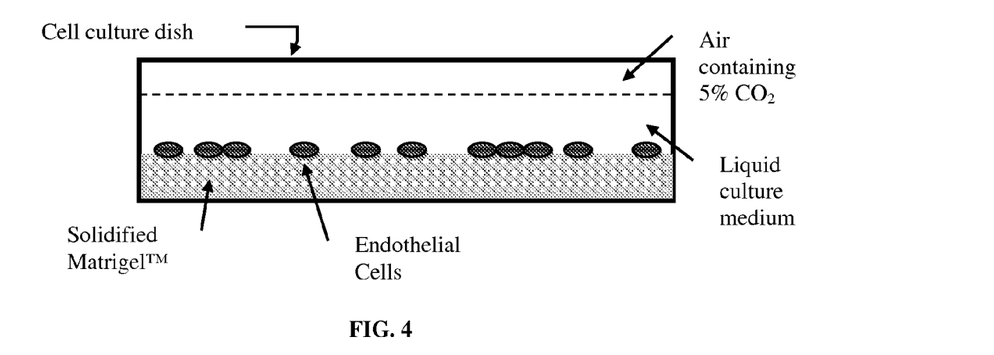
FIG. 4 shows components of a standard two-dimensional Matrigel™ capillary fabrication device. Matrigel™ solidifies at room temperature. Endothelial cells are plated on top of a layer (300-500 µm) of solidified Matrigel™. Cells are covered by about 2 mm of liquid culture medium. A quasi two-dimensional capillary-like network one cell length thick forms on top of the solidified Matrigel™.

Current in vitro capillary fabrication devices are either quasi-two-dimensional or three-dimensional. Quasi-two-dimensional devices are categorized as either rapid or long-term. Rapid quasi-two-dimensional devices consist of a layer of endothelial cells seeded sub-confluently on top of a thick layer of a basement-membrane gel which is made of a mixture of collagen, fibrin, or Matrigel™ Depending on the components and mechanical properties of the gel, endothelial cells align to form a one-cell thick capillary-like pattern within 1 to 3 days. In rapid devices, the standard Matrigel™ capillary fabrication device (FIG. 4) is widely used, especially in assaying applications to characterize anti-angiogenic or pro-angiogenic factors. In the standard quasi-two-dimensional Matrigel™ capillary fabrication device, cells plated on a thick layer (about 0.5 mm) of Matrigel™ are exposed to high levels of soluble and ECM-bound growth factors. A high concentration of growth factors in Matrigel™ (or even Growth Factor Reduced (GFR) Matrigel™) results in artifacts and over-stimulation of cells. Further, cell motility is restricted by adhesion of cells to the solid Matrigel™ and resultant capillaries have endothelial cells that are abnormally elongated compared to the in vivo morphology of endothelial cells. The endothelial cells typically die 24 to 48 hours after forming the networks in rapid quasi-two-dimensional devices (Ranta et al. (1998), *J Cell Physiol.* 176(1):92-98; Vailhé et al. (2001) *Lab Invest.* 81(4):439-452); thus these devices are not suitable for applications requiring viable capillary networks. However, the lumenized capillary networks formed in the devices disclosed herein remain viable for about 4 weeks.

Long-term quasi-two-dimensional devices generally consist of endothelial cells suspended in normal culture medium and conditions without inclusion of an extracellular matrix substrate. As the endothelial cells divide, they form a confluent mono-layer, after which some differentiate spontaneously to form capillary-like structures on top of a confluent layer of undifferentiated endothelial cells. Long-term devices require 2 to 8 weeks of cell culture, making them unsuitable for high-throughput experiments.

Applications of quasi-two-dimensional angiogenesis devices include, for example, studies of the role and synthesis of extracellular matrix in vascular morphogenesis; studies of the roles of adhesion molecules; screening of angiostatic molecules; functional characterization of endothelial cell lines; studies of proteases; extracellular protein synthesis; vessel maturation; and studies of the role of glycation products in diabetes.

Three-dimensional capillary fabrication devices combine endothelial cells with a three-dimensional gel which the endothelial cells then invade. Widely-used three-dimensional in vitro devices include aortic rings in gelified matrices, endothelial cells seeded inside a gel or sandwiched between two layers of gel or between a single layer of gel and a cell-culture surface, and microcarrier beads coated with endothelial cells. The forming capillaries in three-dimensional angiogenesis devices are applied to study the effects of cytokines, metalloproteases and the fibrinolytic pathway during tubulogenesis, endothelial apoptosis, the importance of the configuration and composition of the substrate, the role of cell-adhesion molecules, the effect of hypoxia on endothelial cells, and for screening of angiogenic and angiostatic molecules.

Three-dimensional capillary fabrication devices require many more cells to achieve the cell densities required for fabrication of connected capillary networks. Cell distribution in three-dimensional capillary fabrication devices is not uniform which may cause over-crowded regions and increased cell death. The transport of oxygen and other nutrients to three-dimensional matrices via diffusion limits the thickness of the three-dimensional matrices in those capillary fabrication devices. The cell resources in capillary fabrication devices are prohibitively limited and expensive. Since the cells are embedded in a solidified gel which limits cell motility, the formation of capillary-like patterns is slow, taking 1 to 8 weeks. Thus three-dimensional capillary fabrication devices are inefficient and slow which make them not suitable for industrial, drug-development and high throughput applications.

Thus, improvements are needed for in vitro capillary fabrication devices.

Techniques for the vascularization of tissue-engineered constructs can be broadly grouped into in vitro and in vivo approaches. In vivo approaches rely on vessel ingrowth from host to the engineered tissue. This ingrowth process is often limited to tenths of microns per days, meaning that the time needed for complete vascularization of an implant of several millimeters is in the order of weeks. Several strategies have been developed for improving the ingrowth of vessels from host tissue including scaffold designs, angiogenic-factor delivery and in vivo pre-vascularization. In vitro approaches include in vitro pre-vascularization techniques. In vitro approaches do not rely on ingrowth of host vessels into entire construct. However, anastomosis of the vessels in the in vitro-pre-vascularized tissues is not as fast as in vivo pre-vascularization. In vitro-pre-vascularization also needs to have proper organization and geometry to be able to provide enough blood perfusion after implantation of the engineered tissue.

The capillary fabrication devices disclosed herein can produce highly controlled functional lumenized capillary networks that enhance blood perfusion in the engineered tissue.

Disclosed herein are capillary fabrication devices for manufacturing forming capillary networks and formed capillary networks with natural or controlled geometries the engineered ECM and basement membrane associated with the capillary networks, and application of the capillary networks and ECM and basement membrane for construction of engineered tissues.

The capillary fabrication devices described herein produce capillaries which improve in a number of ways on the standard quasi-two-dimensional Matrigel™ capillary fabrication device. Unlike the standard quasi-two-dimensional Matrigel™ capillary fabrication device, which produces a capillary-like structure composed of unnaturally elongated endothelial cells, the morphology of endothelial cells incorporated in the capillary cords and resulting lumens in the capillary fabrication device described herein are very similar to those in capillaries formed in vivo, e.g., in zebrafish embryos and chick allantois.

Figure 1:
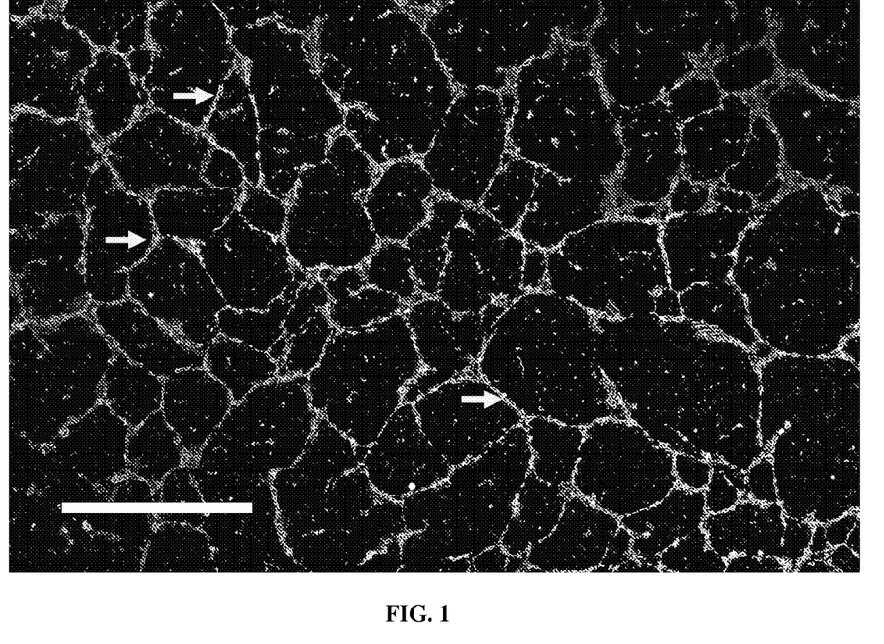
FIG. 1 shows cultured human umbilical vein endothelial cells (HUVECs) after 7 days of culture using the capillary fabrication device. Calcein AM was loaded for fluorescent imaging at 10 µM. White arrows show segments of a viable lumenized capillary network. A typical undifferentiated HUVEC is about 30 µm in vitro. When integrated into a tubule, a typical HUVEC is about 50 to 60 µm. The lumenized capillary lengths range 100 µm to 1500 µm. ECFCs also formed capillaries when cultured using the capillary fabrication device for at least 4 days (not shown).
Figure 2:
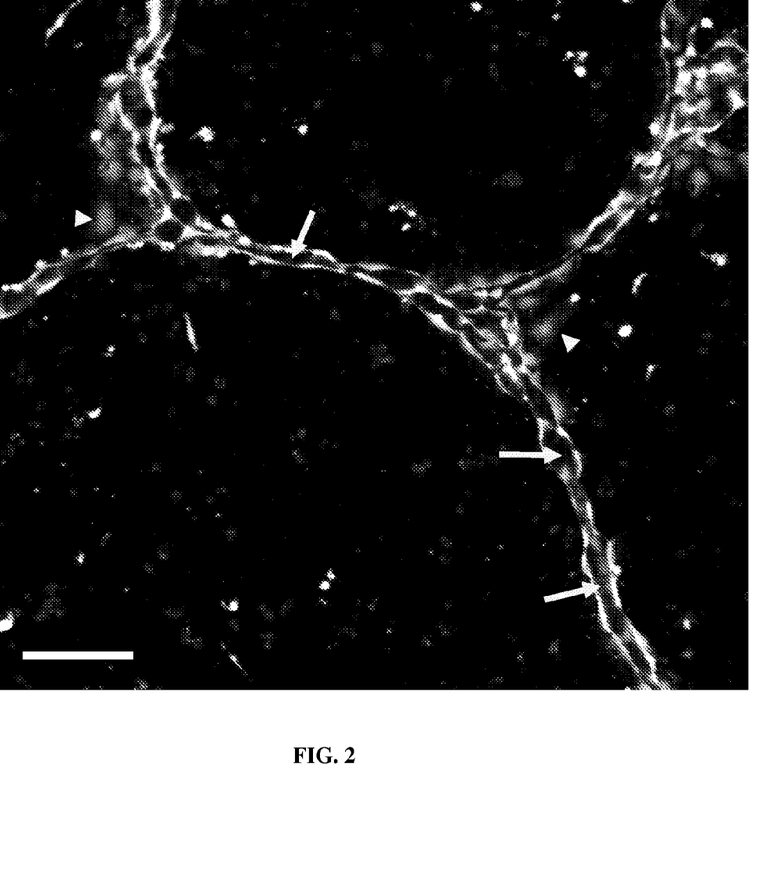
FIG. 2 shows viable lumenized capillary networks formed from HUVECs after 36 hours in the disclosed capillary fabrication device as described herein. They remained viable 7 days later. White arrows show the lumen in the disclosed capillary fabrication device as described herein. The lumenized capillaries have a diameter of 10 to 15 µm. Arrow heads show endothelial cells which have not integrated into the lumenized capillary network. A typical undifferentiated HUVEC is about 30 µm in vitro. When integrated into a tubule, a typical HUVEC is about 50 to 60 µm. Bar, 50 µm.

It has also been found that the standard quasi-two-dimensional Matrigel™ capillary fabrication device (even when growth-factor reduced Matrigel™ is used) produces a honeycomb-like network, in which tubules are often composed of a single endothelial cell stretched and connected to aggregates of endothelial cells. Most capillary tubules formed in the capillary fabrication devices described herein are composed of several cell lengths, and are thus capable of producing mean tubule lengths comparable to capillaries in vivo (FIG. 1). Capillary networks produced using the standard quasi-two-dimensional Matrigel™ capillary fabrication device are not viable for more than 48 hours. The lumenized capillary networks of the capillary fabrication devices described herein may be viable for up to 4 weeks after formation of the network.

The standard quasi-two-dimensional Matrigel™ capillary fabrication device is unable to recapitulate normal cell motility and proliferation since endothelial cells plated on top of a thick layer of Matrigel™ show no or little proliferation and motility. The cells do not have properties that are substantially similar to in vivo cells. For example, mean tubule diameter which has significant biological importance, is usually less than 5 microns in the standard quasi-two-dimensional Matrigel™ capillary fabrication device. Formation of narrow tubes (inner diameter <4 microns) in the standard quasi-two-dimensional Matrigel™ capillary fabrication device also indicates high levels of mechanical stress in the individual cells. Tubes less than 4 microns in diameter do not support natural blood flow. Thus they are non-functional. However, the diameter of engineered lumenized capillaries produced using the capillary fabrication devices described herein were found to range from 5 to 20 microns, which matches the capillary diameters of zebrafish embryos, chick allantois and many human tissues.

In the capillary fabrication devices described herein, only endothelial lineage cells incorporated in capillary cords are not motile and show reduced proliferation potency because of strong junctional complexes; the rest of the cells proliferate and are motile. Thus, the capillary fabrication devices described herein are less sensitive to the seeded cell density than the standard quasi-two-dimensional Matrigel™ capillary fabrication device. This allows formation of capillary networks from limited numbers of stem cells or from an autograft. An autograft capillary network has a lower chance of rejection in tissue repair and engineering applications.

In the capillary fabrication devices described herein, similar to long-term in vitro devices, the lumenized capillary networks remain viable for at least one week after tubulogenesis, and often remain viable for four weeks or more. In contrast, in most in vitro capillary fabrication devices, the capillary-like networks degrade and disappear after tubulogenesis. The longer viability of the engineered capillary networks described herein allows for assays to study the effects of pro/anti-angiogenic factors on both established lumenized capillary networks and the initial stages of tubulogenesis. The steps of endothelial-cell tubulogenesis can be recapitulated in quasi-in vivo conditions.

Use of cell-culture-treated dishes, rather than non-treated dishes, does not produce a capillary-like pattern, but rather increases proliferation of seeded endothelial resulting in a confluent layer of undifferentiated endothelial cells. Typically, normally adherent cells cultured in non-treated polystyrene dishes without coating undergo anoikis/apoptosis after a few hours and die. However, in the capillary fabrication device disclosed herein, the use of a support-generating medium to form the support medium on a non-treated polystyrene surface as a cell-culture surface allows the cells to survive and form capillary networks. Without being bound by theory, it is believed that the binding of specific integrin receptors in the endothelial cells contribute to the initiation of transcription of anti-apoptotic genes, differentiation and tubulogenesis.

Current methods of tissue engineering are limited by the difficulties of forming functional vascular networks in the engineered tissues. Engineered blood vessels using prosthetic conduits are not suitable for vessel diameters of less than 6 mm due to formation of thromboses. Engineered blood vessels which have a lining of endothelial cells, using cell-sheet engineering or bioprinting, are limited to large blood vessels. Thus existing tissue engineering methods are unable to produce functional vascular networks for tissue engineering. The capillary fabrication device and custom-patterned capillary fabrication device are capable of producing functional capillaries which can be integrated with larger vessels in the host tissue or engineered tissue to form functional vascular networks. Engineering thicker metabolically demanding organs, such as heart and liver requires techniques for manufacturing microvessels with highly controlled geometries. Existing microcirculation engineering techniques are not capable of constructing controlled-geometry microvessels capable of connecting to the host vessels, expansion of vascular volume accompanying growing tissue, and prevention of excessive vascular regression. The custom-patterned/controlled-geometry capillary device is capable of producing functional lumenized capillary networks which can highly optimize blood perfusion in the engineered tissue.

In medically-oriented tissue engineering applications autologous resources of cells are limited. Thus engineering tissues from autologous components is often not practical. Extracellular components are highly conserved and known to enhance and regulate growth/regrowth and differentiation of cells in engineered tissues. Use of organically-fabricated ECM and basement membrane (formed using the devices disclosed herein) of non-autologous or non-human (like mouse) origin can be useful for medical tissue-repair and tissue engineering applications with minimal transfer of external factors and thus significant reduction of the likelihood of rejection after implant.

The following various embodiments are provided:

1) A device for fabrication of engineered capillary networks comprising:
living cells;
a cell-culture surface; and
a support-generating medium, the support-generating medium comprising a gel forming material and a liquid cell-culture medium, wherein the gel forming material is substantially dissolved in the cell-culture medium and forms a support medium on the cell-culture surface.

2) A custom-patterned capillary fabrication device comprising:
living cells;
a cell-culture surface; and
a support-generating medium, the support-generating medium comprising a gel forming material and a liquid cell-culture medium, wherein the gel forming material is substantially dissolved in the cell-culture medium and forms a support medium on the cell-culture surface, and wherein the cell-culture surface comprises a network-like pattern containing regions of varying hydrophobicity.

3) The device of any of clauses 1 to 2 wherein the cells are of human origin.

4) The device of any of clauses 1 to 3 wherein the living cells are of endothelial lineage.

5) The device of any of clauses 1 to 4 wherein the cells are selected from the group consisting of embryonic stem cells, endothelial progenitor cells, circulating endothelial cells, and lymphatic endothelial cells.

6) The device of any of clauses 4 to 5 further comprising at least one additional cell type.

7) The device of clause 6 wherein the additional cell type is selected from the group consisting of pericytes, smooth muscle cells, fibroblasts, and any combination thereof.

8) The device of any of clauses 1 to 7 wherein one or more cells are modified cells.

9) The device of any of clauses 1 to 8, wherein the cell-culture surface comprises at least one hydrophobic region.

10) The device of any of clauses 1 to 9 wherein the cell-culture surface comprises a coating of at least one temperature sensitive polymer.

11) The device of clause 10 wherein at least one temperature sensitive polymer is poly(N-isopropylacrylamide).

12) The device of any of clauses 1 to 11 wherein the cell-culture surface is flat.

13) The device of clause 12 wherein the cell-culture surface is selected from the group consisting of petri dishes, well-plates, slides, and coverslips.

14) The device of any of clauses 1 to 13 wherein the cell-culture surface is comprised of a material selected from the group consisting of non-treated polystyrene, glass, a temperature sensitive polymer, and any combination thereof.

15) The device of any of clauses 1 to 14 wherein the cell-culture surface further includes meshes or scaffolds.

16) The device of any of clauses 1 to 15 wherein the cell-culture surface is modified by etching, stamping, contact printing, UV laser ablation, or any combination thereof.

17) The device of any of clauses 1 to 16 wherein the cell-culture medium is a defined cell-culture medium.

18) The device of any of clauses 1 to 16 wherein the cell-culture medium comprises serum albumin.

19) The device of any of clauses 1 to 18 wherein the cell-culture medium comprises a bicarbonate-base or HEPES buffer.

20) The device of any of clauses 1 to 19 wherein the gel-forming material comprises at least one extracellular matrix (ECM) protein.

21) The device of any of clauses 1 to 20 wherein the gel forming material comprises at least one protein selected from the group consisting of laminin, collagen IV, heparan sulfate proteoglycans, entactin/nidogen, TGF-β, epidermal growth factor, insulin-like growth factor, fibroblast growth factor, and tissue plasminogen activator.

22) The device of any of clauses 1 to 20 wherein the gel-forming material is Matrigel™.

23) The device of any of clauses 1 to 20 wherein the support-generating medium comprises Matrigel™ diluted from 1 to 30 to about 1 to 60 times in the liquid cell-culture medium.

24) The device of any of clauses 1 to 20 wherein the support-generating medium is dissolved in the liquid-cell culture medium to yield an ECM protein concentration of from about 170 μg ECM proteins per ml of liquid-cell culture medium to about 350 μg ECM proteins per ml of liquid-cell culture medium.

25) The device of any of clauses 1 to 24 wherein the support medium harbors the living cells.

26) The device of any of clauses 1 to 25 wherein the support medium has a thickness of less than 150 microns.

27) The device of any of clauses 1 to 25 wherein the support medium has a thickness of less than 50 microns.

28) The device of any of clauses 1 to 25 wherein the support medium has a thickness from 50 microns to 100 microns.

29) The device of any of clauses 1 to 25 wherein the support medium has a thickness from 20 microns to 40 microns.

30) A formed capillary network made using the device according to any of clauses 1 to 29.

31) The capillary network of clause 30 wherein the capillary network comprises tubules having a diameter of at least 5 microns.

32) The capillary network of clause 30 wherein the capillary network comprises tubules having a diameter of at least 10 microns.

33) The capillary network of clause 30 wherein the capillary network comprises tubules having a diameter of at least 15 microns.

34) The capillary network of clause 30 wherein the capillary network comprises tubules having a diameter of at least 20 microns.

35) The capillary network of any of clauses 30 to 34 wherein the capillary network geometry is pre-patterned.

36) Use of the device according to any of clauses 1 to 29 to generate a formed capillary network.

37) Use of the device of any of clauses 1 to 29 to generate a forming capillary network.

38) The use according to any of clauses 36 to 37 wherein the living cells are contacted by a test substance suspected to promote or inhibit angiogenesis.

39) An ECM and basement membrane produced by the living cells of the device according to any of clauses 1 to 29, wherein the ECM and basement membrane are detached from a forming or formed capillary network.

40) Use of the device according to any of clauses 1 to 29 to generate an ECM and basement membrane that are detachable from a forming or formed capillary network.

41) The use according to clause 40 wherein the ECM and basement membrane are detached from the capillary network by at least changing the cell-culture temperature.

42) The use according to any of clauses 40 to 41 wherein the ECM and basement membrane are detached from the capillary network by at least changing the pH of the cell-culture medium.

43) The use according to any of clauses 40 to 42 wherein the ECM and basement membrane are detached from the capillary network by at least contacting the capillary network and ECM and basement membrane with a stream of liquid.

44) Use of a capillary network produced by the device of any of clauses 1 to 29 to repair or regenerate tissue in vivo.

45) Use of the ECM and basement membrane of clause 39 in an in vitro tissue engineering application.

46) Use of the ECM and basement membrane of clause 39 in a cell-sheet engineering application.

47) Use of the ECM and basement membrane in a bioprinting application.

BRIEF DESCRIPTION OF THE DRAWINGS

FIG. 3 shows the formation of support medium. After covering the cell-culture surface with support-generating medium containing dissolved gel-forming material, the support-generating medium forms/deposits a loosely-connected support medium. (A), (B), (C), (D) show phase-contrast images of the support medium at 30 minutes, 3 hours, 6 hours and 12 hours after plating. Support medium is the darker patches of material (black arrow-heads in (A) and (B)). Support medium covers the entire surface after about 6 hours (C). Support medium coverage does not change significantly after 6 hours. (D) The support medium after 12 hours. The gray background is the hydrophobic cell-culture surface. Bar, 20 µm.

FIG. 5 shows components of the capillary fabrication device. Support-generating medium which contains a dissolved gel-forming material forms a gel of support medium of about 10 to 30 µm in thickness. Cells are covered by about 2 mm of support-generating medium. Lumenized capillary networks form inside the support medium.

DETAILED DESCRIPTION OF THE ILLUSTRATIVE EMBODIMENTS

For the purposes of promoting an understanding of the principles of the disclosure, reference will now be made to illustrative embodiments. It is understood that no limitation to the scope is intended. It is further understood that any alterations and modifications to the illustrated embodiments and further applications of the principles as may occur to one skilled in the art to which this invention pertains are included within the scope of the disclosure.

As used herein, the phrase "capillary fabrication device" generally refers to a cell-culture which provides an environment for manufacturing capillary-like patterns.

As used herein, the phrase "controlled-geometry capillary fabrication device" or "custom-patterned capillary fabrication device" generally refers to a cell-culture which provides an environment for manufacturing capillary-like networks which have a predefined geometry including tubule lengths, locations and connectivity.

As used herein, the phrase "forming capillary network" generally refers to a group of cells in a capillary fabrication device which are organizing to form one or more tubules.

As used herein, the phrase "formed capillary network" generally refers to a group of cells in a capillary fabrication device which are organized into one or more tubules.

As used herein, the phrase "ECM and basement membrane" generally refers to the extracellular matrix proteins, growth factors, and other components that are associated with the forming or formed capillary networks. The ECM and basement membrane may be produced and/or modified by the cells in the forming or formed capillary network. In general, ECM includes basement membrane which is a laminar organization of extracellular proteins (and associated/other components) including collagen type IV and laminin.

As used herein, the phrase "cell-culture surface" generally refers to a solid which can physically support cells and support medium, and the resulting capillaries.

As used herein, the phrase "non-treated polystyrene" refers to a polystyrene cell culture surface that has not been pre-treated (i.e., prior to contact with the support-generating medium) with an adherence-enhancing substance, corona discharge, gas-plasma, or other like treatments. Likewise, the phrase "cell-culture-treated" refers to cell-culture surfaces providing an adhesive substrate for cell attachment and survival.

As used herein, "patterned surface" refers to a cell-culture surface which has spatially or temporally varying physical or chemical properties including but not limited to hydrophobicity and protein binding affinities. A patterned surface may include glass, biocompatible and biodegradable materials and polymers including but not limited to non-treated polystyrene and temperature sensitive polymers. A patterned surface may include coatings of proteins, polymers, or other materials. A patterned surface may also include scaffolds, meshes and other 2-dimensional or 3-dimensional structures.

As used herein, the phrase "temperature sensitive polymer" refers to a polymer which changes its hydration state depending on temperature. A temperature sensitive polymer includes but is not limited to poly(N-isopropylacrylamide).

As used herein, the phrase "gel-forming material" refers to one or more components that are capable of existing in a gelatinous or high viscosity liquid form. A gel-forming material may include one or more extracellular matrix (ECM) proteins. Extracellular matrix proteins include, but are not limited to, laminin, collagen IV, heparan sulfate proteoglycans, entactin/nidogen, TGF-β, epidermal growth factor, insulin-like growth factor, fibroblast growth factor, and tissue plasminogen activator, and the like. A gel-forming material of extracellular matrix proteins includes but is not limited to Matrigel™.

As used herein, "Matrigel™" refers to a commercially available gelatinous extracellular protein mixture secreted by Engelbreth-Holm-Swarm (EHS) mouse sarcoma cells. Such proteins include laminin, collagen IV, heparan sulfate proteoglycans, entactin/nidogen, TGF-β, epidermal growth factor, insulin-like growth factor, fibroblast growth factor, and tissue plasminogen activator, and additional proteins. Stock Matrigel™ commercially available currently has about 13 mg/ml of protein. Approximately, more than 80 percent of Matrigel™ is ECM proteins. The concentration of ECM proteins is initially about 10.4 mg/ml in Matrigel™ (~80% of 13 mg). Therefore, Matrigel™ stock diluted 1:30 in cell-culture medium (support-generating medium) contains about 347 µg of ECM proteins per ml, and a solution diluted 1:60 contains about 173 µg ECM proteins per ml.

As used herein, "Growth Factor Reduced Matrigel™" (GFR Matrigel™) refers to a commercially available gel that is purified and characterized to a greater extent than standard Matrigel™. GFR Matrigel™ effectively has lower levels of a variety of growth factors except for TGF-beta which may be bound to collagen IV and/or sequestered in a latent form that partitions with the major components in the purification procedure. The major components: laminin, collagen IV and entactin are conserved while the level of heparan sulfate proteoglycan is reduced by about 40-50%.

As used herein, the phrase "liquid cell-culture medium" generally refers to a liquid capable of growing cells and dissolving the gel-forming material. The liquid cell-culture medium may comprise HEPES, or a bicarbonate-based buffer, or other buffer. Optionally, it may also comprise serum albumin.

Figure 5:
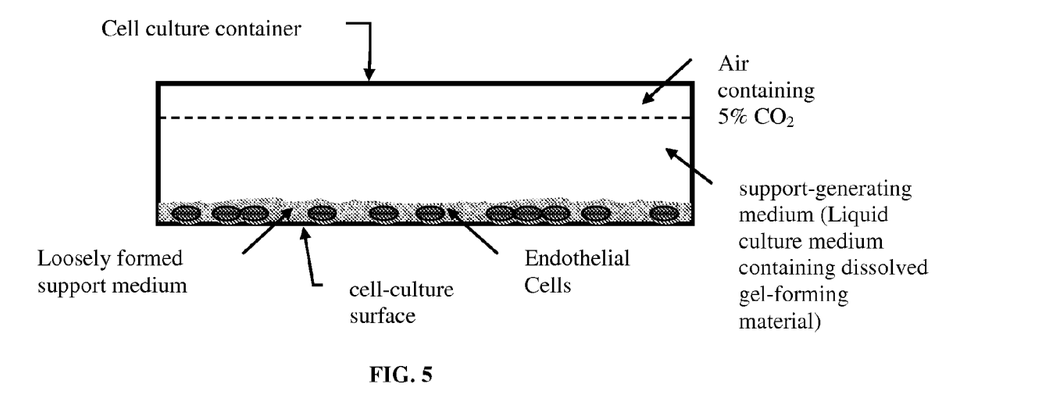
Figure 6:
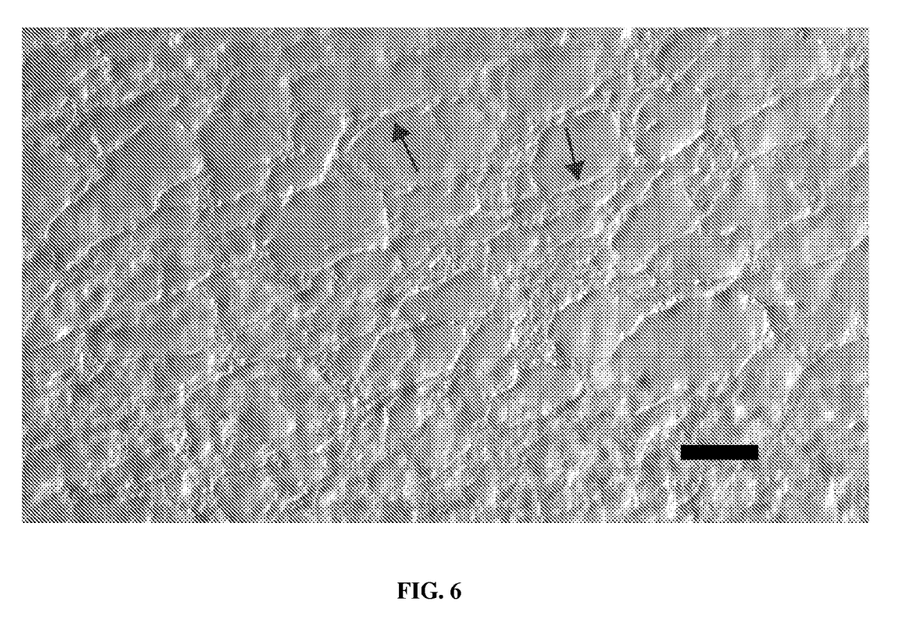
FIG. 6 shows detached ECM generated using a capillary formation device. The ECM was detached from the bottom of a polystyrene dish by making the liquid culture media slightly acidic (pH ~6.0-6.5). Arrows show manufactured cables. Scale bar ~250 µm.

As used herein, the phrase "support-generating medium" refers to a mixture of liquid cell-culture medium and a gel-forming material at low density. The density of the gel-forming material in the support-generating medium is low enough that a substantial portion of the support-generating medium remains in liquid form (i.e. dissolved in the liquid cell-culture medium) throughout the culture period (FIG. 5).

Figure 3:
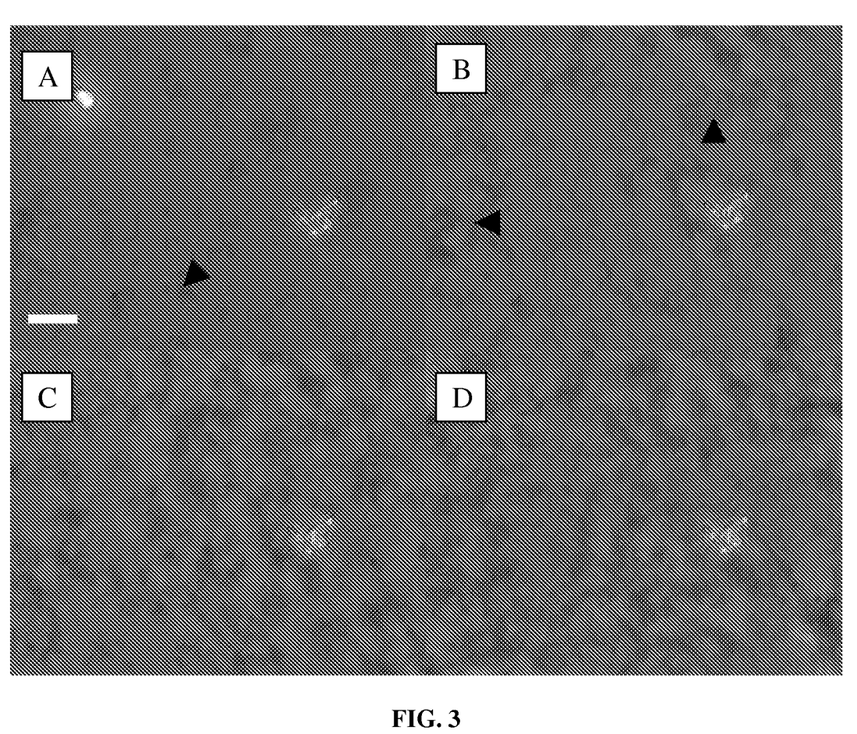

As used herein, the phrases "support medium" or "support matrix" refers to a thin soft gel produced spontaneously by the support-generating medium or by the interaction of the support-generating medium with the cultured cells, or by the interaction of the support-generating medium with the cell-culture surface (FIG. 3).

As used herein, the phrase "endothelial lineage" refers to endothelial cells or precursor cells or their offspring that are capable of differentiating into an endothelial cell. Cells of endothelial lineage include, but are not limited to, endothelial progenitor cells, endothelial colony forming cells, vascular stem cells, embryonic and adult stem cells, circulating endothelial progenitor cells, angioblasts, microvasculature, arteries, veins, and lymphatic endothelial cells of different origin including but not limited to dermal, bladder, cardiac, and pulmonary.

As used herein, "viable" capillaries refer to lumenized capillaries comprising living endothelial cells.

Described herein are devices for fabrication of engineered capillary networks. In various embodiments, the devices comprise living cells, a cell-culture surface, a support-generating medium, and a liquid cell-culture medium. In one illustrative aspect, a gel-forming material is substantially dissolved in the liquid cell-culture medium to form a support-generating medium, which then forms a support medium on the cell-culture surface. As used herein, "substantially dissolved" gel-forming substance means that little or no gel-forming material remains in solid form after the gel forming-material is mixed with the liquid cell-culture medium. The support medium is formed by the support-generating medium or by the interaction of the support-generating medium with the cultured cells, or by the interaction of the support-generating medium with the cell-culture surface. The support medium may partially or completely coat the cell-culture surface. The support medium harbors the living cells. The support medium is not rigid. The support medium permits, growth, motility, and differentiation of living cells. The cells may permeate the support medium as they grow, differentiate, and produce their own ECM and basement membrane.

In one embodiment, the capillary fabrication device has a cell-culture surface that is custom-patterned. In one illustrative aspect, the cell-culture surface pattern is a network-like pattern that contains regions of spatially and/or temporally variable hydrophobicities. In one illustrative aspect, the cell-culture surface comprises hydrophobicity gradients. In one illustrative aspect, the cell-culture surface patterns are linear. In one illustrative aspect, the cell-culture surface patterns are nonlinear. In another illustrative aspect, the cell-culture surface comprises both linear and non-linear patterns.

The cells of the capillary fabrication device may be of human or non-human origin. In one embodiment, the cells are of endothelial lineage. In one embodiment, the cells comprise a plurality of cells types of endothelial lineage. In another embodiment, the cells comprise one or more cell types of endothelial lineage and at least one additional cell type not of endothelial lineage. In one aspect, the cells of non-endothelial lineage provide support and/or stabilize the forming or formed capillary networks. In one illustrative aspect, the additional cell type is selected from the group consisting of pericytes, smooth muscle cells, fibroblasts, and any combination thereof.

In one embodiment, the cells of endothelial lineage or non-endothelial lineage are modified. As used herein, the term "modified cells" includes, but is not limited to, genetic modifications, for example, the insertion, deletion, or change in the expression of a gene or genes in a cell. The term "modified cells" also includes cells affected by any chemical, mechanical, electromagnetic or other modifications made to the culture to modify the cells. Modifications of cells may be made continuously or intermittently at any time before culturing the cells in the capillary fabrication device, and/or during and/or after capillary network formation.

In one embodiment, the capillary fabrication device comprises a cell-culture surface having at least one hydrophobic region. In one illustrative embodiment, the hydrophobic regions form a pattern. In one illustrative aspect, the pattern comprises a hexagonal network of narrow bands of less hydrophilic cell-culture surface having a width of from about 5 microns to about 20 microns, from about 5 microns to about 15 microns, from about 5 microns to about 8 microns, from about 5 microns to about 10 microns, from about 8 microns to about 15 microns, from about 10 microns to about 15 microns, from about 10 microns to about 20 microns, or from about 12 microns to about 20 microns; and a length of from about 175 microns to about 300 microns, from about 200 microns to about 300 microns, from about 175 to about 250 microns, from about 200 to about 250 microns, from about 225 to about 300 microns, or from about 225 to about 25 microns. These various ranges of width and length of the bands are also contemplated where the term "about" is not included. The custom-patterned/controlled-geometry capillaries form on top of the predefined hexagonal network pattern of less hydrophilic cell-culture surface.

In one embodiment, the capillary fabrication devices have a cell-culture surface that is modified to change its hydrophobicity in certain pre-defined regions by application of a hydrophobic substance capable of attracting the cells. Illustratively, the hydrophobic substance may be applied by etching, stamping, contact printing, and the like.

In one embodiment, the cell-culture surface is pre-coated with a layer of a temperature sensitive polymer. The temperature sensitive polymer may become significantly dehydrated at about 37° C. and significantly hydrated at temperatures lower than about 32° C. Illustratively, the polymer coating is more hydrophobic in its hydrated state than in its dehydrated state.

In one embodiment, the temperature sensitive coating is applied to the cell-culture surface in a pre-formed pattern. In another illustrative embodiment, the temperature sensitive coating is applied to the cell-culture surface uniformly and then UV laser ablation is used to pattern the coated surface by reducing the thickness of the coating, thereby reducing the hydrophobicity of that portion of the cell culture-surface. In one illustrative aspect, the temperature sensitive polymer is poly(N-isopropylacrylamide).

In one embodiment of the capillary fabrication devices, the cell culture surface is flat. For example, a flat surface may be a petri dish, well-plate, microscope slide, coverslip, and the like. In one embodiment, the cell-culture surface is comprised of a material selected from the group consisting of non-treated polystyrene, glass, a temperature sensitive polymer, and any combination thereof. Optionally, the cell-culture surface may contain meshes or scaffolds to further pattern the capillary networks in two or three dimensions.

The capillary fabrication devices may comprise any suitable liquid medium for cell culture. Several cell-culture media are known to those of skill in the art. In one embodiment, the cell-culture medium is a defined medium. In one illustrative aspect, the cell-culture medium is bicarbonate based. In one illustrative aspect, the cell-culture medium is HEPES. In one embodiment, the cell-culture medium contains one or more serum proteins. In one illustrative aspect, the cell-culture medium contains serum albumin.

The gel-forming material of the capillary fabrication devices is substantially dissolved in the liquid cell-culture medium to form the support-generating medium. Gel-forming materials for use in the capillary fabrication devices are known to those of skill in the art. In one embodiment, the gel-forming material comprises one or more ECM proteins. Extracellular matrix proteins include, but are not limited to, laminin, collagen IV, heparan sulfate proteoglycans, entactin/nidogen, TGF-β, epidermal growth factor, insulin-like growth factor, fibroblast growth factor, and tissue plasminogen activator, and the like. In one illustrative embodiment, the gel-forming material of the capillary fabrication devices is Matrigel™.

In one embodiment, the support-generating medium comprises Matrigel™ diluted from about 20 to about 80 times, from about 20 to about 60 times, from about 20 to about 40 times, from about 30 to about 80 times, from about 30 to about 60 times, from about 30 to about 45 times, or from about 45 to about 60 times in the liquid cell-culture medium. These various dilutions are also contemplated where the word "about" is not included.

In one embodiment, the support-generating medium of the capillary fabrication devices comprises from about 125 μg to about 500 μg, from about 125 μg to about 170 μg, from about 125 μg to about 250 μg, from about 125 μg to about 350 μg, from about 170 μg to about 350 μg, from about 225 μg to about 350 μg, or from about 170 μg to about 225 μg of ECM proteins per ml of liquid cell-culture medium. These various concentrations are also contemplated where the word "about" is not included.

In the capillary fabrication devices described herein, the support-generating medium forms a support medium after contacting the cell-culture surface and/or the living cells. In one embodiment, the living cells permeate the support medium and reside within the support medium soon after cell plating.

In one embodiment, the capillary fabrication devices comprise a support medium that is less than 150 microns thick. In various other embodiments, the support medium has a thickness of from about 10 microns to about 150 microns, about 10 microns to about 125 microns, about 10 microns to about 100 microns, about 10 microns to about 75 microns, about 10 microns to about 60 microns, about 10 microns to about 50 microns, about 10 microns to about 40 microns, about 20 microns to about 75 microns, about 20 microns to about 60 microns, about 20 microns to about 50 microns, about 30 microns to about 75 microns, about 30 microns to about 60 microns, about 30 to about 50 microns, about 40 microns to about 70 microns, or about 40 microns to about 60 microns. In another embodiment, the support medium has a thickness of from about 20 microns to about 40 microns. In another embodiment, the support medium has a thickness of from about 50 microns to about 100 microns. These various thicknesses are also contemplated where the word "about" is not included. It is appreciated that the thickness of the support medium may not be uniform at all portions of the cell-culture surface.

In one embodiment, a formed capillary network is described made using the capillary fabrication devices described herein. In one illustrative aspect, the formed capillary network comprises tubules and is substantially lumenized. In one illustrative embodiment, the capillary network has a pre-patterned geometry. In one illustrative embodiment, the capillary network comprises tubules having a diameter of at least 5 microns. In another illustrative embodiment, the capillary network comprises tubules having a diameter of at least 10 microns. In one illustrative embodiment, the capillary network comprises tubules having a diameter of at least 15 microns. In one illustrative embodiment, the capillary network comprises tubules having a diameter of at least 20 microns.

In various embodiments, the capillary fabrication devices are used to generate forming or formed capillary networks. In one embodiment, the capillary fabrication devices are used to assess the effects of one or more test substances on angiogenesis. In one illustrative embodiment, the plated cells, or the cells of the forming or formed capillary network are contacted with a test substance suspected to promote or inhibit angiogenesis.

In various embodiments, the ECM and basement membrane produced by the living cells of the capillary fabrication device are detached. The ECM and basement membrane may be detached from the forming or formed capillary networks by various methods. In one illustrative embodiment, the ECM and basement membrane are detached from the capillary network by changing the pH of the cell-culture medium, changing the temperature of the cell-culture medium, contacting the capillary networks and/or ECM and basement membrane with a stream of culture medium, or any combination thereof.

The capillary networks and/or the detached ECM and basement membrane may be used in in vitro tissue engineering applications, for example, cell-sheet engineering, bioprinting, and the like.

The capillary networks and/or detached ECM and basement membrane may also be used in in vivo tissue engineering applications, for example, tissue-repair, tissue regeneration, and the like.

EXAMPLES

Example 1

Sample Capillary Fabrication Devices Using Matrigel™ in the Support-Generating Medium to Culture HUVECs or ECFCs Materials.

Matrigel™ is purchased from BD Biosciences. Single-donor human umbilical cord endothelial cells (HUVECs) are cultured according to protocols provided by PromoCell™. It is recommended to use HUVECs passaged less than 4 times. Alternatively, endothelial colony forming cells (ECFCs) are used. ECFCs may be extracted from human peripheral and umbilical cord blood.

A stock of 1× Matrigel™ is diluted about 30 to about 60 times with about 4° C. cell-culture medium (from PromoCell) to produce a homogeneous support-generating medium. The support-generating medium is plated in non-treated polystyrene petri dishes as the cell-culture surface which has a hydrophobic surface. Components of the mixture settle/stick to the bottom of the dish and form a loosely connected low density environment. About 3 ml of the support-generating medium is enough for 35 mm dishes. The support medium thickness formed on the dish is about 20 to about 40 microns or when Matrigel™ is diluted about 60 times. The support medium thickness formed on the dish is about 50 to about 100 microns or when Matrigel™ is diluted about 30 times. The dishes are incubated for about 30 to about 60 minutes in 5% $CO_2$ at 37° C. in a cell-culture incubator. The culture dishes containing cultured HUVECs and 35 mm dishes of support-generating medium are transferred from the incubator to the cell-culture hood at the same time to minimize heat shock.

After harvesting the cultured HUVECs, the cells are added to the dishes containing the support-generating medium at about 50 to about 300 cells/mm$^2$ to complete the capillary fabrication device. The capillary fabrication device is then incubated in 5% $CO_2$ at 37° C. To produce a fully connected network, cell densities higher than 150 cells/mm$^2$ are used. To distribute the plated HUVECs uniformly, the dishes are gently swirled alternately clockwise and counterclockwise. The support-generating medium is exchanged about every 48 hours with fresh pre-warmed support-generating medium, prepared as above. If the support-generating medium is removed (for example, after about 60 minutes of incubation at 37° C.), and not replenished with support-generating medium, then the HUVECs do not form lumenized capillary networks. After formation of capillary networks, replacing the support-generating medium with regular liquid cell-culture medium may keep the capillaries viable, but formation of new capillaries from cells not integrated in capillaries, may be significantly reduced.

Optionally, the suspended cells may be mixed with the support-generating medium immediately before cell plating (keeping the dilution ratio of Matrigel™ in the support-generating medium between about 1:30 and about 1:60). This procedure eliminates the step of incubating the dishes for about 30 to about 60 minutes and is suited to high-throughput experiments.

Other sources of modified or unmodified cells may be used, including those from human and non-human sources. Endothelial lineage cells may also be used.

Optionally, the cell culture surface may be a flat surface, including but not limited to a well-plate, slide, or coverslip.

A glass culture surface, such as a slide or coverslip, allows for improved high-resolution imaging of the lumenized capillary networks using an inverted or upright microscope for assaying chemical treatments to promote or inhibit vascularization or other purposes.

Optionally, other support/stabilizing cells can be added to the cell culture, including but not limited to pericytes, smooth muscle cells, fibroblasts, myoblasts or any other cell types capable of interacting with or stabilizing the forming or formed lumenized capillary network.

Optionally, modifications to the cells, support-generating medium, or cell-culture surface can be made continuously or intermittently at any time before culturing the cells in the capillary fabrication device, during culturing in the capillary fabrication device and during and after capillary formation and during any subsequent applications. Such modifications are useful in tissue engineering and tissue repair applications which require functional lumenized capillary networks.

Example 2

Sample Custom-Patterned/Controlled-Geometry Capillary Fabrication Devices

In this example, the cell-culture surface in the capillary fabrication device has hydrophobicity gradients. For example, the non-treated polystyrene petri dish in Example 1 can be replaced with a patterned ultra low adhesive polystyrene dish before plating support-generating medium. The ultra low adhesive polystyrene dish provides a cell-culture surface which is more hydrophilic than regular non-treated polystyrene petri dishes. The pattern on the ultra low adhesive polystyrene dish comprises a hexagonal network of narrow bands of 5 to 15 microns in width and 200 to 250 microns in length of less hydrophilic cell-culture surface. Cells of endothelial lineage can be used. The custom-patterned/controlled-geometry capillaries form on top of the predefined hexagonal network pattern of less hydrophilic cell-culture surface.

Optionally, the non-treated polystyrene cell-culture surface in Example 1 can be pre-coated with a layer of temperature sensitive polymers, like poly(N-isopropylacrylamide). The temperature sensitive polymer is dehydrated at 37° C. and hydrated at temperatures lower than 32° C. The polymer coating is more hydrophobic in its hydrated state. The coating hydrophobicity also depends on the thickness of the coating. A coating thickness of more than about 3 nm results in a hydrophobic cell-culture surface at 37° C. The non-treated polystyrene is coated uniformly and then UV laser ablation used to pattern the coated surface by reducing the thickness of the coating according to a customized pattern. The cells in the custom-patterned capillary fabrication device form lumenized capillaries over areas with thinner coating. The cell-culture surface may also be modified by methods including, but not limited to, etching, stamping, and contact printing.

Use of a temperature sensitive polymer in this protocol allows detachment of the formed capillary network and the associated ECM and basement membrane with minimal damage. The cell-culture temperature can be adjusted to facilitate detachment. The detached capillary network and the associated ECM and basement membrane can be used in tissue engineering and tissue repair applications.

The custom-patterned capillary fabrication device is capable of manufacturing capillary networks of specified pattern using cell-culture surfaces with network patterns consisting of narrow bands of 5 to 15 microns in width and specified length and connectivity. The device is capable of producing replicas of 2-dimensional capillary networks like choroidal capillaries in the retina.

Example 3

Sample Capillary Assay Devices

Capillary networks are grown as described in Example 1 using the capillary fabrication device or Example 2 using the custom-patterned capillary fabrication device combined with one or modifications with the aim of determining the effect of those modifications on the cultured cells or on the resulting capillary networks.

The capillary assay device can be used for determining the proangiogenic effects of different isoforms of vascular endothelial growth factor (VEGF) including soluble and ECM-bound isoforms. The cells in the capillary assay device are cultured inside the support medium, thus the device provides quasi-in vivo conditions for the interaction of VEGF isoforms and the cells. Cells in the 2-dimensional standard Matrigel™ capillary fabrication device are cultured on top of a thick solidified gel which differs significantly from in vivo conditions.

The capillary assay device also can be used for determining the effects of various toxic materials such as, for example, lead, arsenic, and the like on angiogenesis. Further, the capillary assay device may be used to study cellular mechanosignaling related to angiogenesis, or the pro/anti angiogenic effects of mechanical stressors such as, for example, ultrasonic waves or altered pressure. Additionally, the capillary assay device may be used to study the pro/anti angiogenic effects of magnetic or electric fields, or electromagnetic waves.

Example 4

Engineered Capillary Networks with Modified Cells

Cells used in this example can be modified before, during or after growth of capillary network using the capillary fabrication device (Example 1) or the custom-patterned capillary fabrication device (Example 2). After a sufficient period of growth, the capillaries are detached in a manner causing minimal or no damage to the capillary network and can be used for in vivo or in vitro implantation.

The capillary networks formed using custom-patterned capillary fabrication device (Example 2) have predefined geometry which makes them suitable for tissue engineering and repair applications with specified geometries and metabolic rates.

In vitro modification of cells used to grow the capillary networks may be useful in minimizing the chance of rejection in allotransplantation or xenotransplantation.

Example 5

Engineered ECM and/or Basement Membrane

Capillary networks are grown as described in Example 1 using the capillary fabrication device or Example 2 using the custom-patterned capillary fabrication device. After a sufficient period of growth, the cells are destroyed, for example, by washing the capillary network with a liquid, for example, distilled water, while retaining the ECM and basement membrane. Then the patterned ECM and basement membrane are detached in a manner causing minimal or no damage to the capillary network, for example, by using a stream of culture media, or by using temperature sensitive polymers. Adjusting the temperature or pH to modify hydrophobicity can facilitate detachment. For example, adjusting the pH of the culture media to slightly acidic (pH ~6-6.5) is found to facilitate detachment of ECM.

The thickness of the ECM may be controlled by the concentration of the support-generating medium. For example, using diluted Matrigel™ as a gel-forming material, the thickness of manufactured ECM is about 20 to 40 microns when Matrigel™ is diluted at a ratio of 1:60 and about 50 to 100 microns when diluted at a ratio of 1:30. The ECM has a net-work like morphology. The support matrix is organized in cables that are about 50 to 500 microns long when cultured for 5 days using a 1:30 dilution of Matrigel™. The width of the cables is about 15 to 100 microns. The length of the cables increases over the duration of the culture period. For example, cables about 1.5 mm long are observed after 10 days of culture. At more dilute concentrations (e.g. Matrigel™ at 1:60) the cables elongate faster. Thus, the dilution of the gel forming material and duration of culture can be controlled to generate ECM with customized morphology.

The cell-remodeled basement membrane and ECM may then be used to enhance growth/regrowth of vasculature in vivo or in vitro. In vivo implantation can be examined.

After in vivo implantation of the cultured ECM and/or basement membrane, regrowth of capillaries and pericyte recruitment occurs as cells invade the empty sleeves of basement membrane and/or ECM left behind by the destroyed capillaries. Since extracellular components are highly conserved, this organically-manufactured basement membrane/ECM is useful for medical tissue-repair applications with minimal transfer of external factors and thus significant reduction of the likelihood of rejection after implant.

The engineered ECM and basement membrane using custom-patterned capillary fabrication devices (Example 2) have predefined geometry which makes them suitable for growth/regrowth of vasculature in tissue engineering and tissue repair applications with specified geometries and metabolic rates.

Example 6

Use of Engineered ECM and Basement Membrane in Cell-Sheet Engineering and Bioprinting In this example quasi-two-dimensional layers of engineered ECM and basement membrane (Example 5) are placed in horizontal layers separated by 100 to 200 micron layers of engineered tissue in cell-sheet engineering and bioprinting applications. The resulting enhanced growth of capillary networks in cell-sheet engineering and bioprinting applications results in a functional vascular network to provide blood flow to all volumes of the engineered tissue, enhancing the likelihood of integration of engineered 3-dimensional tissues.

Example 7

Use of Implantable Capillary Networks in Cell-Sheet Engineering and Bioprinting

In this example quasi-two-dimensional layers of formed or forming capillary networks and associated ECM and basement membrane (Example 4) formed using the capillary fabrication device or custom-patterned fabrication device are placed in horizontal layers separated by 100 to 200 micron layers of engineered tissue in cell-sheet engineering and bioprinting applications. Integration of the capillary networks with existing or engineered larger vessels in these applications results in a functional vascular network to provide blood flow to all volumes of the engineered tissue, enhancing the likelihood of integration of engineered 3-dimensional tissues.

Example 8

Formation and Patterning of Hydrophobic Domains on the Cell Culture Surface

Highly hydrophobic domains in the culture surface coating are generated with polydimethylsiloxane (PDMS) which the cells do not populate. Moderately hydrophobic domains, which cells invade and populate, are generated with long carbon chain silanes, for example trichloro(octyl)silane, trichloro(decyl)silane, trichloro(dodecyl)silane, trichloro(octadecyl)silane, trimethoxy(octyl)silane, trimethoxy(decyl)silane, trimethoxy(dodecyl)silane, trimethoxy(octadecyl)silane, triethoxy(octyl)silane, triethoxy(decyl)silane, triethoxy(dodecyl)silane, or triethoxy(octadecyl)silane. Photoresist masking may be used to generate patterns of moderately hydrophobic and highly hydrophobic domains on the cell culture surface.

For example, a clean glass slide is functionalized with one or more long carbon silanes (moderately hydrophobic) to create a carbon chain monolayer. The slide is exposed in a 0.2-2% silane in organic solvents (e.g. methanol, acetone, toluene, heptane, carbon tetrachloride, xylene, and the like) followed by a methanol rinse and then dried under nitrogen gas. The surface is then spin-coated with a thin, approximately 5-10 μm layer of positive photoresist (e.g. SPR220, PMMA, and the like). After softbaking the substrate is exposed to UV light through a mask with a spatial pattern to be replicated by the cells of the functionalized glass substrates. After removing the exposed photoresist a thin layer of PDMS is spin-coated on. The PDMS is then etched by tetrabutylammonium fluoride (TBAF) solution in tetrahydrofuran (THF) until the layer becomes 2-5 μm thick. The substrates are then briefly exposed to UV light without any mask. The photoresist domains masked during the prior exposure are removed, revealing the silane coated glass domains surrounded by PDMS domains.

Example 9

HUVECs do not Invade Highly Hydrophobic PDMS Domains

Figure 7:
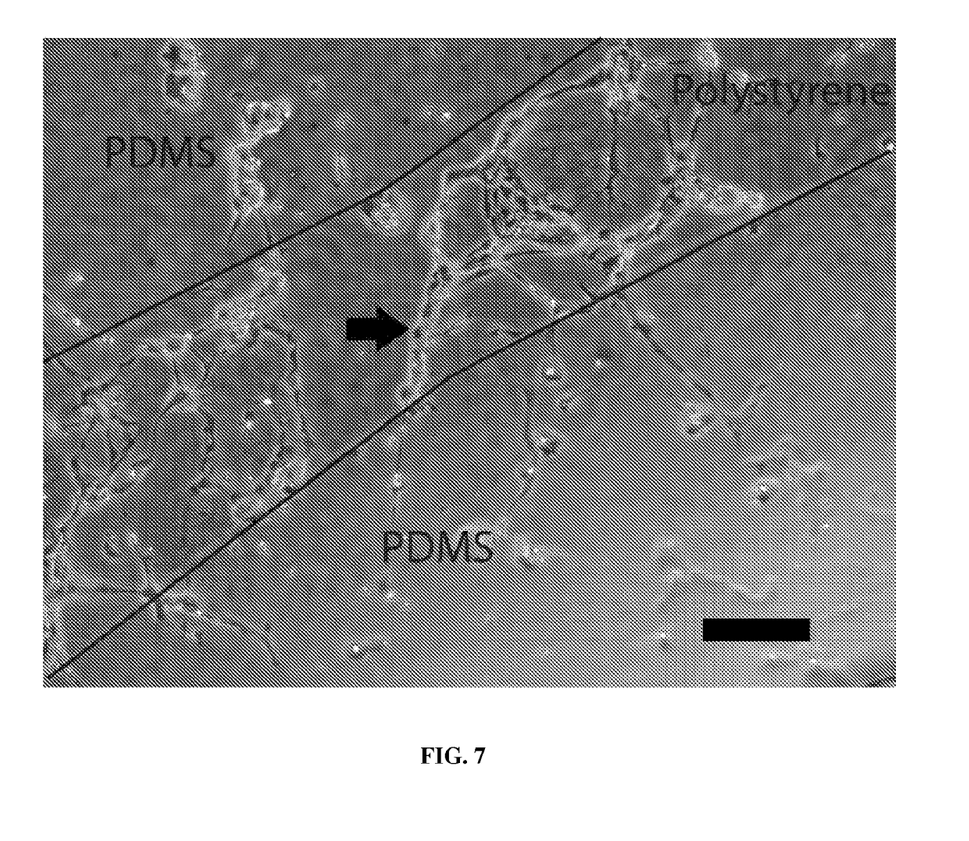
FIG. 7 shows the formation of capillaries by HUVECs cultured on a polystyrene dish having regions coated with support medium and regions coated with highly hydrophobic PDMS. HUVECs grew and formed capillary networks on the polystyrene coated with support medium but did not grow and form networks on regions coated with PDMS. The boundary between PDMS regions and polystyrene (with support medium) regions are demarcated by two black lines. The black arrow shows a formed capillary. Scale bar ~250 µm.

A capillary fabrication device is utilized to culture HUVECs as described in Example 1. A PDMS coating is applied as described in Example 8 to a polystyrene surface. The HUVECs grow and form capillaries on a polstyrene surface containing a support medium, but do not grow on regions of the surface coated with PDMS (FIG. 7).

Example 10

Implantation of Viable Capillary Networks

Capillary networks formed using the capillary fabrication devices are implanted ex ovo. Chicken eggs are incubated for 3 days at 37° C. On day 3, eggs are broken and embryos are transferred to 10 cm dishes. The embryos are grown for 3-4 more days. On day 6-7, capillary networks formed by HUVECs are implanted in up to four regions of chorioallantoic membrane (CAM). The CAMs are scratched with a sharp needle until a small amount of blood appears. The capillaries are then injected into the CAM using a micro-pipette.

The capillary networks are labeled with Calcein AM to examine their viability. Calcein AM is used as an indicator of viability because it diffuses out of cells when they die. Implanted capillary networks are viewed under microscope after implantation. Viable implanted HUVEC cells are observed 2 days after implantation.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present invention.

What is claimed is:

1. A custom-patterned capillary fabrication device comprising:
a capillary network of living cells;
a non-treated polystyrene cell-culture surface; and
a low-density support-generating medium, the low-density support-generating medium comprising a gel forming material and a liquid cell-culture medium in a ratio of 1:30 to 1:60, wherein the gel forming material is substantially dissolved in the liquid cell culture medium and forms a support medium having a thickness of between 20 microns and 100 microns on the non-treated polystyrene cell-culture surface, wherein the non-treated polystyrene cell-culture surface comprises a network-like pattern containing regions of varying hydrophobicity, and wherein the gel-forming material is Matrigel.

2. The device of claim 1 wherein the living cells are selected from the group consisting of stem cells, endothelial progenitor cells, circulating endothelial cells, and lymphatic endothelial cells.

3. The device of claim 2 further comprising at least one additional cell type selected from the group consisting of pericytes, smooth muscle cells, fibroblasts, and any combination thereof.

4. The device of claim 1, wherein the non-treated polystyrene cell-culture surface comprises at least one hydrophobic region.

5. The device of claim 1 wherein the non-treated polystyrene cell-culture surface comprises a coating of at least one temperature sensitive polymer.

6. The device of claim 1 wherein the non-treated polystyrene cell-culture surface is modified by etching, stamping, contact printing, UV laser ablation, or any combination thereof.

7. The device of claim 2 wherein the liquid cell-culture medium comprises one or more components selected from the group consisting of serum albumin, a bicarbonate-base, a HEPES buffer, and an extracellular matrix (ECM) protein.

8. The device of claim 1 wherein the gel forming material comprises at least one protein selected from the group consisting of laminin, collagen IV, heparan sulfate proteoglycans, entactin/nidogen, TGF-β, epidermal growth factor, insulin-like growth factor, fibroblast growth factor, and tissue plasminogen activator.

9. The device of claim 1 wherein the gel-forming material is dissolved in the liquid cell-culture medium to yield an ECM protein concentration of from 170 μg ECM proteins per ml of liquid cell-culture medium to 350 μg ECM proteins per ml of liquid cell-culture medium.

10. The device of claim 1 wherein the support medium harbors the living cells.

11. The device of claim 1 wherein the support medium has a thickness from 20 microns to 40 microns.

12. The device of claim 1, wherein the capillary network of living cells comprises vacuolized living cells.

13. A custom-patterned capillary fabrication device comprising:
a capillary network of living cells comprising vacuolized living cells;
a non-treated polystyrene cell-culture surface; and a low-density support-generating medium having a thickness of between 20 microns and 100 microns, the low-density support-generating medium comprising Matrigel and a liquid cell-culture medium in a ratio of 1:30 to 1:60, wherein Matrigel is substantially dissolved in the cell-culture medium and forms a support medium on the cell-culture surface, and wherein the non-treated polystyrene cell-culture surface comprises a network-like pattern containing regions of varying hydrophobicity, and wherein the support medium comprises extracellular matrix proteins in a concentration of from 170 μg extracellular matrix proteins per ml of liquid cell-culture medium to 350 μg extracellular matrix proteins per mL of liquid cell-culture medium.

* * * * *